(12) United States Patent
MacKinnon et al.

(10) Patent No.: US 8,100,826 B2
(45) Date of Patent: *Jan. 24, 2012

(54) APPARATUS AND METHODS RELATING TO EXPANDED DYNAMIC RANGE IMAGING ENDOSCOPE SYSTEMS

(75) Inventors: Nicholas B. MacKinnon, Vancouver (CA); Ulrich Stange, Vancouver (CA)

(73) Assignee: Tidal Photonics, Inc., Vancouver, British Columbia (CA)

( * ) Notice: Subject to any disclaimer, the term of this patent is extended or adjusted under 35 U.S.C. 154(b) by 152 days.

This patent is subject to a terminal disclaimer.

(21) Appl. No.: 12/433,733

(22) Filed: Apr. 30, 2009

(65) Prior Publication Data

US 2010/0004513 A1 Jan. 7, 2010

Related U.S. Application Data

(63) Continuation of application No. 10/951,448, filed on Sep. 27, 2004, now Pat. No. 7,544,163.

(60) Provisional application No. 60/506,273, filed on Sep. 26, 2003.

(51) Int. Cl.
*A61B 1/06* (2006.01)

(52) U.S. Cl. ......... 600/178; 600/160; 600/109; 362/574

(58) Field of Classification Search .................. 600/160, 600/178, 109; 362/574; 356/326, 328
See application file for complete search history.

(56) References Cited

U.S. PATENT DOCUMENTS

| | | | |
|---|---|---|---|
| 4,158,505 A | 6/1979 | Mathisen et al. |
| 4,175,545 A | 11/1979 | Termanini |
| 4,204,528 A | 5/1980 | Termanini |
| 4,401,124 A | 8/1983 | Guess et al. |
| 4,407,294 A | 10/1983 | Vilkomerson |
| 4,511,229 A | 4/1985 | Schwartz et al. |
| 4,582,061 A | 4/1986 | Fry |

(Continued)

FOREIGN PATENT DOCUMENTS

AU 2002231504 B2 2/2002

(Continued)

OTHER PUBLICATIONS

Supplementary European Search Report Dated Jul. 1, 2010, for European Patent Application No. EP 04 78 6670.

(Continued)

*Primary Examiner* — John P Leubecker
(74) *Attorney, Agent, or Firm* — Joshua King; Graybeal Jackson LLP

(57) ABSTRACT

The apparatus and methods herein provide quantitatively controllable light sources and expanded dynamic range endoscopy systems that can improve the quality of images and the ability of users to distinguish desired features when viewing tissues by providing methods and apparatus that improve the dynamic range of images from endoscopes, in particular for example with endoscopes that have dynamic range limited because of small image sensors and small pixel electron well capacity, and other optical system constraints. The apparatus and methods herein, for example, combine light sources with quantitatively variable spectral output and quantitatively variable wavelength dependent intensity distribution with image sensors and controllers to create an expanded dynamic range endoscopy system. By digitally combining illumination data from the digitally controllable light source with the digital image data from the image sensor the system synthesizes expanded dynamic range images whose dynamic range exceeds the dynamic range of the image sensor alone thus providing greatly enhanced information content in the acquired images.

17 Claims, 9 Drawing Sheets

U.S. PATENT DOCUMENTS

| | | |
|---|---|---|
| 4,706,681 A | 11/1987 | Breyer et al. |
| 4,739,396 A | 4/1988 | Hyatt |
| 4,763,993 A | 8/1988 | Vogeley et al. |
| 4,782,386 A | 11/1988 | Ams et al. |
| 4,843,529 A | 6/1989 | Izenour |
| 4,848,880 A | 7/1989 | Aull et al. |
| 4,858,001 A | 8/1989 | Milbank et al. |
| 4,867,563 A | 9/1989 | Wurm et al. |
| 4,885,634 A | 12/1989 | Yabe |
| 4,890,208 A | 12/1989 | Izenour |
| 4,937,448 A | 6/1990 | Mantz et al. |
| 4,955,385 A | 9/1990 | Kvalo et al. |
| 5,037,173 A | 8/1991 | Sampsell et al. |
| 5,090,807 A | 2/1992 | Tai |
| 5,092,331 A | 3/1992 | Nakamura et al. |
| 5,121,239 A | 6/1992 | Post |
| 5,172,146 A | 12/1992 | Wooldridge |
| 5,187,572 A | 2/1993 | Nakamura et al. |
| 5,233,459 A | 8/1993 | Bozler et al. |
| 5,256,869 A | 10/1993 | Lin et al. |
| 5,259,837 A | 11/1993 | Van Wormer |
| 5,270,797 A | 12/1993 | Pollak et al. |
| 5,305,083 A | 4/1994 | Marianik et al. |
| 5,351,151 A | 9/1994 | Levy |
| 5,369,481 A | 11/1994 | Berg et al. |
| 5,409,000 A | 4/1995 | Imran |
| 5,409,009 A | 4/1995 | Olson |
| 5,432,543 A | 7/1995 | Hasegawa et al. |
| 5,440,388 A | 8/1995 | Erickson |
| 5,461,475 A | 10/1995 | Lerner et al. |
| 5,474,519 A | 12/1995 | Bloomer |
| 5,528,368 A | 6/1996 | Lewis et al. |
| 5,555,085 A | 9/1996 | Bogdanowicz et al. |
| 5,587,832 A | 12/1996 | Krause |
| 5,604,566 A | 2/1997 | Mano et al. |
| 5,748,308 A | 5/1998 | Lindberg et al. |
| 5,754,278 A | 5/1998 | Kurtz |
| 5,796,508 A | 8/1998 | Suzuki |
| 5,805,213 A | 9/1998 | Spaulding et al. |
| 5,828,485 A | 10/1998 | Hewlett |
| 5,926,773 A | 7/1999 | Wagner |
| 5,938,319 A | 8/1999 | Hege |
| 6,046,808 A | 4/2000 | Fateley |
| 6,075,563 A | 6/2000 | Hung |
| 6,110,106 A | 8/2000 | MacKinnon et al. |
| 6,128,077 A | 10/2000 | Jovin et al. |
| 6,128,078 A | 10/2000 | Fateley |
| 6,191,802 B1 | 2/2001 | Kessler |
| 6,204,941 B1 | 3/2001 | Beale et al. |
| 6,265,708 B1 | 7/2001 | Tanaka et al. |
| 6,303,916 B1 | 10/2001 | Gladnick |
| 6,337,760 B1 | 1/2002 | Huibers et al. |
| 6,339,429 B1 | 1/2002 | Schug |
| 6,356,378 B1 | 3/2002 | Huibers |
| 6,369,933 B1 | 4/2002 | O'Callaghan |
| 6,412,972 B1 | 7/2002 | Pujol et al. |
| 6,436,127 B1 | 8/2002 | Anderson et al. |
| 6,437,919 B1 | 8/2002 | Brown et al. |
| 6,459,919 B1 | 10/2002 | Lys et al. |
| 6,464,633 B1 | 10/2002 | Hosoda et al. |
| 6,485,414 B1 | 11/2002 | Neuberger |
| 6,490,017 B1 | 12/2002 | Huang et al. |
| 6,504,943 B1 | 1/2003 | Sweatt et al. |
| 6,545,758 B1 | 4/2003 | Sandstrom |
| 6,567,163 B1 | 5/2003 | Sandstrom |
| 6,567,217 B1 | 5/2003 | Kowarz et al. |
| 6,567,543 B1 | 5/2003 | Shiraiwa et al. |
| 6,618,184 B2 | 9/2003 | Jin et al. |
| 6,646,633 B1 | 11/2003 | Nicolas |
| 6,654,048 B1 | 11/2003 | Barrett-Lennard et al. |
| 6,654,493 B1 | 11/2003 | Hilliard et al. |
| 6,657,758 B1 | 12/2003 | Garner |
| 6,663,560 B2 | 12/2003 | MacAulay et al. |
| 6,710,909 B2 | 3/2004 | Naito |
| 6,781,691 B2 | 8/2004 | MacKinnon et al. |
| 6,806,954 B2 | 10/2004 | Sandstrom |
| 6,824,283 B2 | 11/2004 | Pohlert et al. |
| 6,842,549 B2 | 1/2005 | So |
| 6,859,275 B2 | 2/2005 | Fateley et al. |
| 6,873,727 B2 | 3/2005 | Lopez et al. |
| 6,878,109 B2 | 4/2005 | Yamaki et al. |
| 6,882,770 B2 | 4/2005 | Neilson et al. |
| 6,900,825 B2 | 5/2005 | Kito |
| 6,909,377 B2 | 6/2005 | Eberl |
| 6,909,459 B2 | 6/2005 | Watson, Jr. et al. |
| 6,996,292 B1 | 2/2006 | Gentry et al. |
| 7,019,908 B2 | 3/2006 | Van 'T Spijker et al. |
| 7,106,435 B2 | 9/2006 | Nelson |
| 7,108,402 B2 | 9/2006 | MacKinnon et al. |
| 7,151,601 B2 | 12/2006 | MacKinnon et al. |
| 7,196,789 B2 | 3/2007 | Senturia et al. |
| 7,224,335 B2 * | 5/2007 | Gibbon et al. .................. 345/84 |
| 7,274,500 B2 | 9/2007 | Kowarz |
| 7,342,658 B2 | 3/2008 | Kowarz et al. |
| 7,511,871 B2 | 3/2009 | MacKinnon et al. |
| 7,544,163 B2 | 6/2009 | MacKinnon et al. |
| 7,599,550 B1 | 10/2009 | Kaplinsky |
| 7,692,784 B2 | 4/2010 | MacKinnon et al. |
| 7,796,319 B2 | 9/2010 | MacKinnon et al. |
| 2001/0052977 A1 | 12/2001 | Toyooka |
| 2002/0057431 A1 | 5/2002 | Fateley et al. |
| 2002/0113881 A1 | 8/2002 | Funston et al. |
| 2002/0156349 A1 | 10/2002 | Yamaki et al. |
| 2002/0161283 A1 | 10/2002 | Sendai |
| 2002/0176151 A1 | 11/2002 | Moon et al. |
| 2002/0180973 A1 | 12/2002 | MacKinnon et al. |
| 2003/0030801 A1 | 2/2003 | Levenson et al. |
| 2003/0107732 A1 | 6/2003 | Sasaki et al. |
| 2003/0135092 A1 | 7/2003 | Cline et al. |
| 2003/0142274 A1 | 7/2003 | Gibbon et al. |
| 2003/0174324 A1 | 9/2003 | Sandstrom |
| 2003/0187330 A1 | 10/2003 | Abe |
| 2004/0218172 A1 | 11/2004 | DeVerse et al. |
| 2004/0233448 A1 | 11/2004 | Goulas et al. |
| 2005/0063079 A1 | 3/2005 | MacKinnon et al. |
| 2005/0213092 A1 | 9/2005 | MacKinnon et al. |
| 2005/0234302 A1 | 10/2005 | MacKinnon et al. |
| 2005/0251230 A1 | 11/2005 | MacKinnon et al. |
| 2008/0212980 A1 | 9/2008 | Weiner |
| 2008/0260242 A1 | 10/2008 | MacKinnon et al. |

FOREIGN PATENT DOCUMENTS

| | | |
|---|---|---|
| AU | 2007200111 A1 | 2/2007 |
| AU | 2007205778 A1 | 8/2007 |
| CA | 2404600 A1 | 10/2001 |
| CA | 2388696 A1 | 2/2002 |
| CA | 2474832 A1 | 8/2002 |
| CA | 2380765 A1 | 10/2002 |
| CA | 2461599 A1 | 4/2003 |
| CA | 2581656 A1 | 4/2005 |
| CA | 2581660 A1 | 4/2005 |
| CA | 2581668 A1 | 4/2005 |
| CA | 2581697 A1 | 4/2005 |
| CA | 2581735 A1 | 4/2005 |
| EP | 0008639 A1 | 3/1980 |
| EP | 1304019 A1 | 4/2003 |
| EP | 1360438 A2 | 11/2003 |
| EP | 1656584 A2 | 5/2006 |
| EP | 1709405 A1 | 10/2006 |
| EP | 1709474 A1 | 10/2006 |
| EP | 1709475 A1 | 10/2006 |
| EP | 1709476 A1 | 10/2006 |
| EP | 1713540 A2 | 10/2006 |
| GB | 2377280 A | 1/2003 |
| JP | 04-297225 | 10/1992 |
| JP | 06207853 | 7/1994 |
| JP | 08185986 | 7/1996 |
| JP | 11056758 | 3/1999 |
| JP | 11101944 | 4/1999 |
| JP | 11295219 | 10/1999 |
| JP | 2000504115 | 4/2000 |
| JP | 2000195683 | 7/2000 |
| JP | 2003010101 | 1/2003 |
| JP | 2003248181 A | 9/2003 |
| JP | 2004526188 | 8/2004 |
| JP | 2001208985 | 5/2005 |
| JP | 2007-506994 | 3/2007 |

| | | |
|---|---|---|
| JP | 2007506485 | 3/2007 |
| JP | 2007506486 | 3/2007 |
| JP | 2007506487 | 3/2007 |
| JP | 2007506947 | 3/2007 |
| JP | 2007-534973 | 11/2007 |
| WO | 9852386 A | 11/1998 |
| WO | 0182778 A2 | 11/2001 |
| WO | WO 0201921 | 1/2002 |
| WO | 02063206 A2 | 8/2002 |
| WO | 03029791 A1 | 4/2003 |
| WO | WO 2005010597 | 2/2005 |
| WO | 2005030328 A2 | 4/2005 |
| WO | 2005031292 A1 | 4/2005 |
| WO | 2005031433 A1 | 4/2005 |
| WO | 2005031436 A1 | 4/2005 |
| WO | WO 2005031434 A1 | 4/2005 |

OTHER PUBLICATIONS

Cohen (Jul. 24, 1998) "Spatial Light Modulator Technologies for WDM" (Ph.D. Thesis); Univeristy of Cambridge; Cambridge, England, UK; pp. 155-161.

Neto et al. (Aug. 10, 1996) "Full-Range, Continuous, Complex Modulation by the Use of Two Coupled-Mode Liquid-Crystal Televisions"; Applied Optics; Optical Society of America; 35 (23):4567.

Office Action Dated Apr. 12, 2010, European Patent Office, for European Patent Application No. 04 786 667.8.

International Search Report, PCT/CA2004/001751, Feb. 16, 2005.

Office Action Dated Jun. 15, 2010, Japanese Patent Office, for Japanese Patent Application No. 2006-527248 (English Translation Provided).

Office Action Dated Mar. 10, 2010, Canadian Intellectual Property Office, for Canadian Patent Application No. 2,474,832.

Supplemental European Search Report Dated Nov. 26, 2009, for European Patent Publication No. EP 1709474 Published Oct. 11, 2006.

Canadian Patent Office—PCT, International Search Report, International Application No. PCT/CA2004/001748, Feb. 16, 2005, 2 pages.

U.S. Appl. No. 11/496,960, filed Jul. 31, 2006, titled, "Apparatus and Methods Relating to Wavelength Conditioning of Illumination," Inventors: Nicholas B. MacKinnon, Calum E. MacAulay, Ulrich Stange, now abandoned.

U.S. Appl. No. 11/725,987, filed Mar. 19, 2007, titled, "Apparatus and Methods Relating to Wavelength Conditioning of Illumination," Inventors: Nicholas B. MacKinnon, Calum E. MacAulay, Ulrich Stange, now abandoned.

U.S. Appl. No. 11/983,752, filed Nov. 9, 2007, titled, "Apparatus and Methods Relating to Wavelength Conditioning of Illumination," Inventors: Nicholas B. MacKinnon, Calum E. MacAulay, Ulrich Stange, now abandoned.

U.S. Appl. No. 12/176,269, filed Jul. 18, 2008, titled, "Apparatus and Methods Relating to Wavelength Conditioning of Illumination," Inventors: Nicholas B. MacKinnon, Calum E. MacAulay, Ulrich Stange, now abandoned.

U.S. Appl. No. 12/242,671, filed Sep. 30, 2008, titled, "Apparatus and Methods Relating to Wavelength Conditioning of Illumination," Inventors: Nicholas B. MacKinnon, Calum E. MacAulay, Ulrich Stange.

U.S. Appl. No. 12/072,493, filed Feb. 25, 2008, titled, "Apparatus and Methods Relating to Color Imaging Endoscope Systems," Inventors: Nicholas B. MacKinnon and Ulrich Stange.

U.S. Appl. No. 12/197,988, filed Aug. 25, 2008, titled, "Apparatus and Methods for Performing Phototherapy, Photodynamic Therapy and Diagnosis," Inventors: Nicholas B. MacKinnon and Ulrich Stange.

European Patent Office, International Search Report, International Application No. PCT/CA02/00124, Aug. 19, 2002, 3 pages.

Canadian Patent Office—PCT, International Search Report, International Application No. PCT/CA2004/001749, Feb. 23, 2005, 8 pages.

Canadian Patent Office—PCT, International Search Report, International Application No. PCT/CA2004/001762, Feb. 16, 2005, 3 pages.

Davidson et al. (1999) Optical Society of America, 24(24):1835.

International Search Report, International Application No. GB0207826.9, Dated Oct. 30, 2002.

International Search Report, International Application No. PCTCA2004001752, Dated Feb. 16, 2005.

International Search Report, International Application No. PCTUS2004022977, Dated Oct. 4, 2006.

Office Action, U.S. Appl. No. 10/061,966, Dated Nov. 20, 2003.

U.S. Appl. No. 60/506,273, filed Sep. 26, 2003, Titled, "Apparatus and Methods Relating to Expanded Dynamic Range Imaging Endoscope Systems," Now Expired.

U.S. Appl. No. 11/473,506, filed June 22, 2006, Titled, "Apparatus and Methods for Measuring and Controlling Illumination for Imaging Objects, Performances and the Like," Now Abandoned.

U.S. Appl. No. 11/709,340, filed Feb. 20, 2007, Titled, "Apparatus and Methods for Measuring and Controlling Illumination for Imaging Objects, Performances and the Like," Now Abandoned.

* cited by examiner

APPARATUS AND METHODS RELATING TO EXPANDED DYNAMIC RANGE IMAGING ENDOSCOPE SYSTEMS

CROSS-REFERENCE TO RELATED APPLICATIONS

The present application claims priority from pending U.S. provisional patent application No. 60/506,273 filed Sep. 26, 2003.

BACKGROUND

The diagnosis and treatment of disease often requires a device to view the interior passages of the body or body cavities that may have to be accessed by surgical instruments. The most common way to do this is via endoscopy systems. Endoscopes are well known as devices to relay images of the internal anatomy to the eye of a physician or surgeon. They include flexible endoscopes such as bronchoscopes, gastroscopes, colonoscopes, sigmoidoscopes and others. They also include rigid endoscopes such as arthroscopes, laparoscopes, cystoscopes, uretoscopes and others. Endoscopes may use optical, fiberoptic or electronic devices or systems to relay images to the operator. Endoscopes are typically part of an imaging system. The imaging system usually comprises light sources, cameras, image recording devices and image display devices such as video monitors or printers.

Endoscopes have become smaller and less expensive to build and have resulted in a continuing improvement in image quality. Newer and smaller imaging sensors such as charge coupled devices (CCDs) or complementary metal oxide semiconductor (CMOS) image sensors have allowed the cameras to record and transmit a video image to be integrated into the tip of the endoscope.

A problem with integrating these image sensors into the small space available at the tip of an endoscope is that compromises in either image resolution or image dynamic range are usually required. Resolution is the ability to spatially resolve details in an image. Dynamic range refers to range of shades of light and dark that can be captured by the imaging device. A limiting factor for resolution is usually not the optical quality of the endoscope lenses but the number of pixels available on the CCD. A limiting factor for dynamic range is the ability of each pixel of the CCD to capture the light that makes up an image. Smaller image sensors require smaller pixels, and smaller pixels mean less ability to capture a wide range of light levels.

Most endoscopes are equipped with image sensors that can capture a color image when the tissue is illuminated by white light. This is usually accomplished by placing optical filters that transmit different colors over adjacent pixels on the image sensor. Usually these filters are red, green and blue filters, but they may also be other colors such as cyan, yellow and magenta, or other combinations of colors as may be desired. These filters are commonly arranged in a repeating spatial pattern wherein filters of different colors are located over pixels adjacent to one another. A common pattern of red, green and blue pixels is a Bayer pattern. The adjacent color filtered pixels are each assigned the same spatial location in the digital image, even though they are not actually in the same location and thus the features of the image they are measuring are not in the identical spatial location. Usually these pixels are close enough to approximate the optical characteristics of the tissue being imaged, but they may in some cases reduce the ability to accurately locate details, such as networks of blood vessels. In contrast, when the detector's pixels are actually measuring the same location in the image the measurement can be more accurate.

One method of improving the accuracy of imaging can be to use three image sensors maintained at the proximal end of the endoscope. Such sensors split the image into three wavelength components, each with its own image path, so that the images are registered accurately on each image sensor. These types of image sensors are commonly called 3-CCD cameras and are commercially available from companies such as Sony Corporation of Japan. These devices are feasible and produce high quality images when the endoscope relays an optical image outside of the body cavity, rather than transmitting an electronic image, but are costly and cannot be easily implemented in the tip of an endoscope.

Another method of producing high quality images is to use a single monochrome CCD and to sequentially capture images illuminated by different wavelengths of illumination light by changing a filter in front of the sample or target. Such systems have been produced using optical filter wheels as with an endoscope system produced by Pentax Corporation of Japan and have also been produced using liquid crystal color filters or acousto-optic tunable filters placed in front of cameras, such as those available from QImaging Corporation of Vancouver, Canada. While the liquid crystal and acousto-optic filters have good control of exposure time, none are currently available placed at the tip of an endoscope.

Endoscopes with monochrome CCDs have been produced and used in conjunction with rotating filter wheels by Pentax Corporation but these have the disadvantage of fixed exposure duration and fixed relative brightness provided by the filters in the rotating filter wheel.

A more common method of producing endoscopy images has been the integration of matrix filtered CCD or CMOS image sensors in the tip of an endoscope. In order to make the image sensor small enough to fit in the tip of a small endoscope compromises are typically made in the number and size of the pixels available. Pixels are usually reduced to the smallest practical size manufacturable. When the pixels are made smaller, the capacity to capture photons of light is proportionally reduced to loss of the active area of the pixel, and the ability to capture wide ranges of brightness is also reduced. The ability to capture wide ranges of brightness is in part reduced because, in the case of the most common type of image sensor, when the photon is captured in the silicon of the device, it generates electrons which must be stored until they can be read out and measured. The smaller the pixel, the fewer electrons strike it and the fewer it can store, so the more limited the range of brightness that it can measure. If the image projected on the sensor by the endoscope objective varies greatly in brightness, the entire range of information will not be captured and some parts of the image will be too bright while other parts are too dark.

Thus, there has gone unmet a need for endoscopy cameras and endoscopy systems that can improve the performance of endoscopes by improving image qualities such as contrast and dynamic range. The present apparatus and methods provide these and other advantages.

SUMMARY

The apparatus and methods herein provide light sources and endoscopy systems, etc., that can improve the quality of endoscopes and the ability of users to distinguish desired features with endoscopes.

The endoscopy systems comprise an endoscope with an integrated image sensor such as a video camera at the distal tip or portion of the endoscope. Generally speaking, the distal end of an endoscope is the end of the endoscope that is inserted into the body and directed to a target tissue; the proximal end is the end of the endoscope that is maintained outside the body, and typically comprises an ocular eyepiece and one or more handles, knobs and/or other control devices that allow the user to manipulate the distal end of the endoscope or devices located at the distal end of the endoscope. As used herein, the distal end of the endoscope includes the distal tip of the endoscope, which is the most distal surface or opening of the endoscope, and the portion of the endoscope adjacent to the distal tip of the endoscope. Endoscopes generally are well known. U.S. Pat. No. 6,110,106; U.S. Pat. No. 5,409,000; U.S. Pat. No. 5,409,009; U.S. Pat. No. 5,259,837; U.S. Pat. No. 4,955,385; U.S. Pat. No. 4,706,681; U.S. Pat. No. 4,582,061; U.S. Pat. No. 4,407,294; U.S. Pat. No. 4,401,124; U.S. Pat. No. 4,204,528; U.S. Pat. No. 5,432,543; U.S. Pat. No. 4,175,545; U.S. Pat. No. 4,885,634; U.S. Pat. No. 5,474,519; U.S. Pat. No. 5,092,331; U.S. Pat. No. 4,858,001; U.S. Pat. No. 4,782,386; U.S. Pat. No. 5,440,388.

Endoscopes usually further comprise an illumination light guide, typically an optical fiber, fiber bundle, lens or combination of these or other optical relay systems, that transmits light from a light source and projects it to illuminate the anatomical site being imaged.

In a video-endoscope the video camera can be an imaging sensor such as a complementary metal-oxide semiconductor (CMOS) or charge coupled device (CCD) image sensor, a charge injection device (CID), or a photodiode array, and an objective lens that forms an image of the anatomical site on the image sensor. The image sensor is usually a color image sensor with a matrix of color filters superimposed on the sensor but may be a monochrome image sensor without a matrix of color filters superimposed on the sensor.

The image sensor can be operated under computer or other electronic control and may or may not be synchronized with a light source. The image output may be a digital or an analog image.

The apparatus and methods herein provide a computer controlled light source and image processing system that works interactively to produce images with expanded dynamic range, improved image contrast and improved image quality.

The computer controlled light source embodiments comprise a lighting system that comprises a bright source of broad-band visible illumination commonly called white light, a wavelength dispersive element such as a prism or diffraction grating and a reflective pixelated spatial light modulator (RPSLM). The light from the light source is directed as a beam to the wavelength dispersive element which disperses the beam into a spectrum that is imaged onto a RPSLM. The pixel element of the RPSLM can be switched to select wavelengths of light and selected amounts of the selected wavelengths of light to propagate. The light that propagates is then, if desired, optically mixed together and directed to the illumination path of an endoscope or other medical or non-medical device.

The RPSLM may be operably connected to a controller, which controller contains computer-implemented programming that controls the on/off pattern of the pixels in the RPSLM. The controller can be located in any desired location to the rest of the system.

In one aspect, the present apparatus and methods provide a lighting system that provides a variable selected spectral output and a variable selected wavelength dependent intensity distribution. The lighting system comprises a light path that comprises: a) a spectrum former configured to provide a spectrum from a light beam traveling along the light path, and b) a reflective pixelated spatial light modulator (RPSLM) located downstream from and optically connected to the spectrum former, the RPSLM reflecting substantially all light impinging on the RPSLM and switchable to reflect light from the light beam between at least first and second reflected light paths, at least one of which does not reflect back to the spectrum former. The RPSLM can be a digital micromirror device. The RPSLM is operably connected to at least one controller containing computer-implemented programming that controls an on/off pattern of pixels in the RPSLM to reflect a desired segment of light in the spectrum to the first reflected light path and reflect substantially all other light in the spectrum impinging on the RPSLM to at least one of the second reflected light path and another reflected light path that typically does not reflect back to the spectrum former, the desired segment of light consists essentially of a desired selected spectral output and a desired wavelength dependent intensity distribution.

In some embodiments, the system further comprises a light source located upstream from the spectrum former, and the spectrum former comprises at least one of a prism and a diffraction grating, which can be a reflective diffraction grating, transmission diffraction grating, variable wavelength optical filter, or a mosaic optical filter. The system may or may not comprise, between the spectrum former and the RPSLM, an enhancing optical element that provides a substantially enhanced image of the spectrum from the spectrum former to the RPSLM. The RPSLM can be a first RPSLM, and the desired segment of light can be directed to a second RPSLM operably connected to the same controller or another controller containing computer-implemented programming that controls an on/off pattern of pixels in the second RPSLM to reflect the desired segment or other segment of light in one direction and reflect other light in the spectrum in at least one other direction. The system can further comprise an optical projection device located downstream from the first RPSLM to project light out of the lighting system as a directed light beam.

The desired segment of light can, for example, be selected to substantially mimic a spectral output and a wavelength dependent intensity distribution of at least one of the output energy for disease treatment, photodynamic therapy, or disease diagnosis, or to enhance contrast for detection or discrimination of a desired object in a sample.

In another aspect, the present apparatus and methods provides a stand alone light source that is sized to project light onto a tissue and having a variable selected spectral output and wavelength dependent intensity distribution. The source of illumination can comprise a) a high output light source, b) a spectrum former optically connected to and downstream from the light source to provide a spectrum from a light beam emitted from the light source, c) an enhancing optical element optically connected to and downstream from the spectrum former that provides an enhanced image of the spectrum; d) a RPSLM located downstream from and optically connected to the spectrum former, the RPSLM reflecting substantially all light impinging on the RPSLM and switchable between at least first and second reflected light paths, wherein the RPSLM can be operably connected to at least one controller containing computer-implemented programming that controls an on/off pattern of pixels in the RPSLM to reflect a desired segment of light in the spectrum in first reflected light path and reflect other light in the spectrum to at least one of the second reflected light path and another reflected light path that does not reflect back to the spectrum former, the desired segment of light consisting essentially of a desired selected spectral output and a desired wavelength dependent intensity distribution; and, e) a projection system optically connected to and downstream from the RPSLM in the first direction, wherein the projection system projects the desired segment as a directed light beam to illuminate the tissue.

The source of illumination can further comprise a detector optically connected to and downstream from the RPSLM, the detector also operably connected to a controller containing computer-implemented programming configured to determine from the detector whether the desired segment contains a desired selected spectral output and a desired wavelength dependent intensity distribution, and adjust the on/off pattern of pixels in the RPSLM to improve the correspondence between the desired segment and the desired selected spectral output and the desired wavelength dependent intensity distribution. The source of illumination can also comprise a heat removal element operably connected to the light source to remove undesired energy emitted from the light source toward at least one of the RPSLM, the enhancing optical element, and the spectrum former. The various aspects, embodiments, elements, etc., discussed herein can be combined and permuted as desired. For example, the sources of illumination and lighting systems, as well as methods, kits, and the like related to them, etc., can comprise various elements discussed for each other even if the elements are specifically discussed only for the other (for example, the detector of the source of illuminations can also be suitable for use with the lighting system).

The heat removal element can be located between the spectrum former and the first reflective spatial light modulator, between the lamp and the spectrum former, or elsewhere as desired. The heat removal element can comprise a dichroic mirror. The dichroic mirror can transmits desired wavelengths and reflects undesired wavelengths, or vice-versa. The undesired energy can be directed to an energy absorbing surface and thermally conducted to a radiator. The heat removal element can be an optical cell containing a liquid that absorbs undesired wavelengths and transmits desired wavelengths. The liquid can be substantially water and can flow through the optical cell via an inlet port and outlet port in a recirculating path between the optical cell and a reservoir. The recirculating path and the reservoir can comprise a cooling device, which can be a refrigeration unit, a thermoelectric cooler, or a heat exchanger.

The source of illumination further can comprise a spectral recombiner optically connected to and located downstream from the pixelated spatial light modulator, which can comprise a prism, a Lambertian optical diffusing element, a directional light diffuser such as a holographic optical diffusing element, a lenslet array, or a rectangular light pipe. In one embodiment, the spectral recombiner can comprise an operable combination of a light pipe and at least one of a lenslet array and a holographic optical diffusing element. A detector can be located in the at least one other direction, and can comprise at least one of a CCD, a CID, a CMOS, and a photodiode array. The high output light source, the spectrum former, the enhancing optical element that provides an enhanced image, the RPSLM, and the projection system, can all be located in a single housing, or fewer or more elements can be located in a single housing.

In another aspect the light source or endoscopy system comprises an adapter or other apparatus for mechanically and/or optically connecting the illumination light guide of an endoscope to the output of the light source. The illumination light guide of the endoscope can be at least one of an optical fiber, optical fiber bundle, liquid light guide, hollow reflective light guide, or free-space optical connector or other light guide as desired. The light guide may be integral with the remainder of the endoscope or it may be modular and separable from the endoscope.

In another aspect the endoscope comprises a longitudinal tube of a biologically compatible and suitable material such as stainless steel or a suitable polymer that may be inserted into the body and that is equipped with an objective lens, and an image sensor and a light output port at the distal tip of the endoscope, typically sealed or encapsulated for cleaning or sterilization. The objective lens and/or the illumination path may comprise a beam steering mirror or prism or other beam director for side or angle viewing of a tissue. The endoscope may further provide a lumen that provides for insertion of a tissue sampling accessory such as a brush or biopsy forceps, or a treatment accessory such as an electrosurgical loop or optical fiber or other accessory.

In some embodiments the image sensor of the endoscope can be an unfiltered image sensor. An unfiltered image sensor relies on the natural optical response of the sensor material to light impinging on the sensor to generate an image signal.

In other embodiments the image sensor can have an optical filter placed in front of it to limit the wavelengths of light that reach the sensor. Unlike a matrix filter that only allows selected wavelengths to reach selected pixels, the optical filter is configured to allow the same wavelengths to reach all pixels if they are present in the signal from the sample. The optical filter can be at least one of a long-pass filter, a short-pass filter, a band-pass filter, or a band-blocking filter. In some embodiments of the apparatus and methods the image sensor of the endoscope can be an unfiltered image sensor. An unfiltered image sensor relies on the natural optical response of the sensor material to light impinging on the sensor to generate an image signal.

In other embodiments of the apparatus and methods the image sensor can have an optical filter placed in front of it to limit the wavelengths of light that reach the sensor. It may also have a matrix filter that only allows selected wavelengths to reach selected pixels. The optical filter can be at least one of a long-pass filter, a short-pass filter, a band-pass filter, or a band-blocking filter. The matrix optical filter can be at least two of a long-pass filter, a short-pass filter, a band-pass filter, or a band-blocking filter. A long-pass filter is useful to block undesired wavelengths such as ultraviolet light or fluorescence excitation light from impinging on the sensor. A short-pass filter is useful to block undesired wavelengths such as infrared light from impinging on the sensor. A band-pass filter may be useful to allow only selected wavelengths such as visible light to impinge on the detector. A band-blocking filter is useful to block fluorescence excitation light from impinging on the image sensor.

The light source and sensor are operably connected to a controller that contains computer-implemented programming that controls the time of image acquisition in the image sensor and the wavelength distribution and duration of illumination in the light source. The controller can be located in any desired location relative to the rest of the system. For example, the controller can be either within a housing of the source of illumination or it can be located remotely, connected by a wire, fiber optic cable, cellular link or radio link to the rest of the system. If desired, the controller, which is typically a single computer but can be a plurality of linked computers, a plurality of unlinked computers, computer chips separate from a full computer or other suitable controller devices, can also contain one or more computer-implemented programs that provide control of image acquisition and/or control of specific lighting characteristics, i.e., specific desired, selected spectral outputs and wavelength dependent intensities, corresponding to known wavelength bands that are suitable for imaging or a specific light for disease diagnosis or treatment, or to invoke disease treatment (for example by activating a drug injected into a tumor in an inactive form), or other particular situations. In another embodiment of the apparatus and methods, the computer controlled image sensor (CCIS) can be synchronized to the computer controlled light source (CCLS) to provide sequences of color images of tissue illuminated by desired wavelengths of light and captured as digital images. These digital images can then be combined or processed as desired to provide useful information to the physician or surgeon.

In one embodiment of the apparatus and methods, the endoscopy system or CCLS provides an image capture device or sub-system able to accept a digital or analog video image signal provided by an existing commercial endoscopy video system or a custom video system constructed in a similar manner to an existing commercial video system. The image capture device may be integral to the CCLS or it may be a modular component of an endoscopy system. It may be operably connected to a controller containing computer implemented programming.

The endoscopy system can further comprise computer controlled image acquisition and processing systems that can analyze the information from an image or sequence of images and present it in a way that is meaningful to an operator.

In another embodiment of the apparatus and methods, the controller contains computer implemented programming that can analyze the image of the tissue captured from the image sensor and if desired adjust the intensity of the illumination of the tissue to provide an image that is enhanced for the operating range of the sensor. If desired, the systems can then apply the information to adjust the illumination of the tissue to scale the captured color image in a way to suitably present the resultant image while restoring the appropriate relationships between the intensities of the pixels in the color image channels and while expanding the dynamic range of the image. The illumination of the tissue can enhance the contrast of a desired anatomical feature, for instance a blood vessel or a cancerous lesion, and the information can be used to adjust the illumination of the tissue to scale the captured color image in a way suitable to present the resultant image in a useful or meaningful way.

The CCLS and CCIS may be operably connected to a controller, which controller contains computer-implemented programming that controls image acquisition in the CCIS and the wavelength distribution and duration of illumination in the CCLS.

The methods further can comprise passing the modified light beam by an optical projection device located downstream from at least one of the first RPSLM and the second RPSLM to project light as a directed light beam. The methods may or may not comprise passing the spectrum by an enhancing optical element between the spectrum former and the pixelated spatial light modulator.

The methods can further-comprise reflecting the desired segment of light to a detector optically connected to and downstream from the RPSLM, the detector located in the second reflected light path or otherwise as desired and operably connected to the controller, wherein the controller contains computer-implemented programming configured to determine from the detector whether the desired segment contains the desired selected spectral output and the desired wavelength dependent intensity distribution, and therefrom determining whether the first segment contains the desired selected spectral output and the desired wavelength dependent intensity distribution. The methods can comprise adjusting the on/off pattern of pixels in the RPSLM to improve the correspondence between the desired segment and the desired selected spectral output and the desired wavelength dependent intensity distribution.

The methods can also comprise removing undesired energy emitted from the light source toward at least one of the RPSLM, the enhancing optical element, and the spectrum former, the removing effected via a heat removal element operably connected to the light source. The methods further can comprise a spectral recombiner optically connected to and located downstream from the RPSLM.

The methods can further comprise directing the output beam to illuminate a tissue by at least one of directly illuminating the tissue via a projected beam, or directing the beam into the light guide of an endoscope, or directing the beam into the light guide of a surgical microscope or other imaging system for viewing tissue.

The methods can further comprise capturing an image of the light emitted by a tissue illuminated by the light from the CCLS and storing it for processing, analysis or display.

The methods can further comprise combining a sequence of digital or analog images and processing or combining them to form an image of the tissue that provides information to the physician or surgeon.

The methods can comprise capturing and displaying a sequence of images from a monochrome imager sensor where the wavelengths of illumination are substantially in the red, green and blue portions of the wavelength spectrum (or in the cyan, yellow and magenta portions of the wavelength spectrum) and the images are combined to produce a color image with the red, green and blue channels.

The methods can further comprise capturing an image from a color image sensor such as an image sensor equipped with a Bayer filter, and analyzing the image of the tissue captured from the image sensor and if desired adjusting the intensity of the illumination of the tissue to provide an image that is optimized for the operating range of the sensor.

The methods can further comprise capturing an image from a color image sensor such as an image sensor equipped with a Bayer filter, analyzing the image of the tissue captured from the image sensor and if desired adjusting the intensity of the illumination of the tissue to provide an image that is optimized for the operating range of the sensor, and then applying the information used to adjust the illumination of the tissue to scale the captured color image in a way suitable to present the resultant image while restoring the appropriate relationships between the intensities of the pixels in the color image channels and while expanding the dynamic range of the image.

The methods can further comprise capturing an image from a color image sensor such as an image sensor equipped with a Bayer filter, analyzing the image of the tissue captured from the image sensor and if desired adjusting the intensity of the illumination of the tissue to provide an image that is optimized to enhance the contrast of a desired anatomical feature, for instance a blood vessel or a cancerous lesion, and then applying the information used to adjust the illumination of the tissue to scale the captured color image in a way suitable to present the resultant image in a useful or meaningful way.

In another aspect, the present invention further comprises a light source located upstream from the input port. The light source may be a laser, a Xenon arc lamp, a mercury arc lamp, a tungsten filament lamp, a metal halide lamp, a fluorescent lamp, an infrared source, a gas discharge tube, a light emitting diode, or any other kind of light source that can be shaped into a light beam. These and other aspects, features and embodiments are set forth within this application, including the following Detailed Description and attached drawings. The discussion herein provides a variety of aspects, features, and embodiments; such multiple aspects, features and embodiments can be combined and permuted in any desired manner. In addition, various references are set forth herein that discuss certain apparatus, systems, methods, or other information; all such references are incorporated herein by reference in their entirety and for all their teachings and disclosures, regardless of where the references may appear in this application. Such incorporated references include: U.S. Pat. No. 6,781,691; pending U.S. patent application Ser. No. 10/893,132, entitled Apparatus And Methods Relating To Concentration And Shaping Of Illumination, filed Jul. 16, 2004, now abandoned; United States patent publication No. US-2005-0234302, published Oct. 20, 2005, entitled Apparatus And Methods Relating To Color Imaging Endoscope Systems, filed contemporaneously herewith; United States patent publication No. US-2005-0251230, published Nov. 10, 2005, entitled Apparatus And Methods For Performing Phototherapy, Photodynamic Therapy And Diagnosis, filed contemporaneously herewith; United States patent publication No. US-2005-0213092, published Sep. 29, 2005, entitled Apparatus And Methods Relating To Enhanced Spectral Measurement Systems, filed contemporaneously herewith.

DETAILED DESCRIPTION

Figure 1:
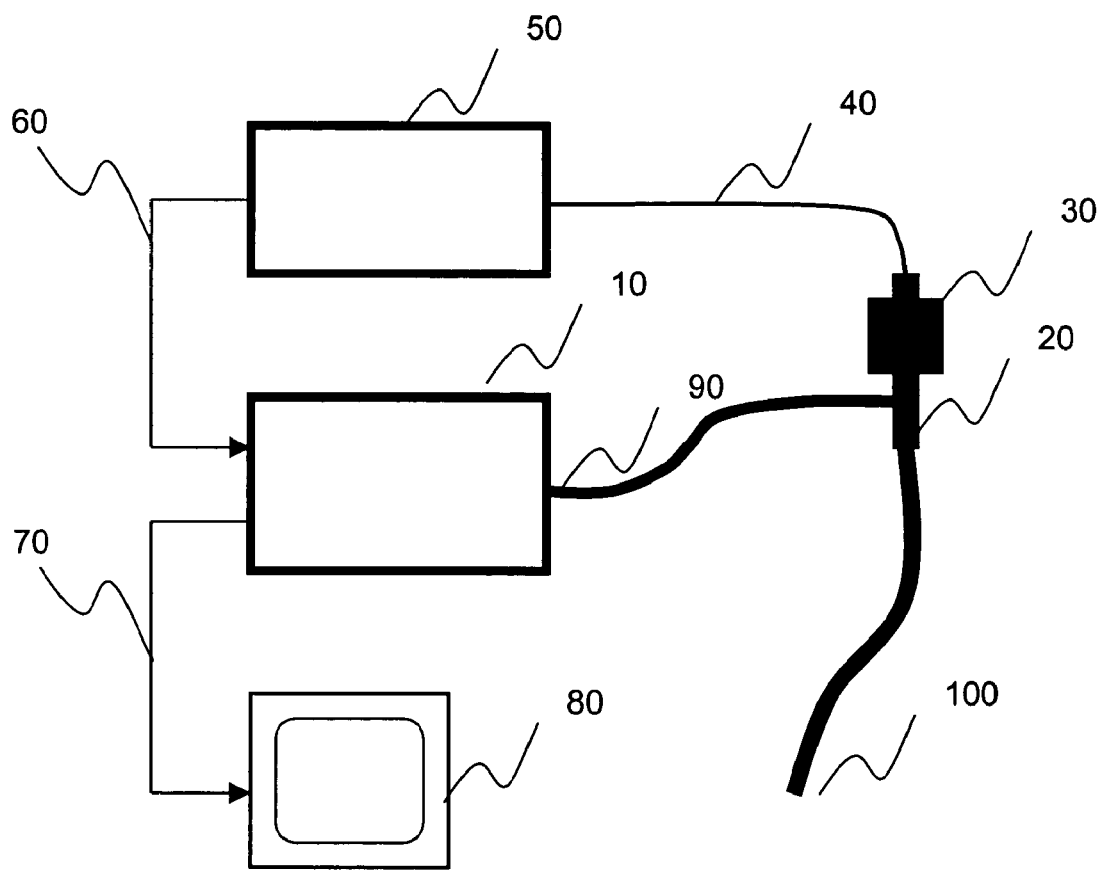
FIG. 1 provides a schematic depiction of a computer controlled "tunable" light source that can change the wavelength dependent distribution of illumination energy, equipped with an integrated image capture device and connected to an endoscope, camera control unit and camera and image display system.

One of the problems in medical imaging is when an imaging device over- or under-exposes the target tissue. This is somewhat like overexposing or underexposing a picture taken with a normal camera, and means that the image is too light or dark to properly see the target tissue. In medical situations, however, this failure can be critically important because it can hide a cancer or injury. Previously, systems have handled this problem by turning up or down the total amount of light shone on the sample. In order to reduce this problem, the present invention comprises tunable light sources that can selectively turn the power up or down, whether only in a single wavelength band, a plurality of bands, or overall. This is advantageous, for example, because often the overexposure is due to only a single wavelength band of light, not the overall illumination power, so the overexposed band is corrected (thereby providing the full information for that band) while the remainder of the light is unchanged (so that the full information from those bands isn't lost due to the underexposure in such bands caused by turning down the total light intensity. The tunable light sources are used in combination with sensitive detectors and computers that control and measure both how much the light source is turned up or down and how much light returns from the sample, and then combines them to provide images that cover a much wider overall range of intensities and valuable information. This reduces the chance that the tissue appears overexposed or underexposed (this is known as improving the dynamic range of the endoscope). The systems, methods, etc., herein provide significantly improved imaging systems for endoscopes, surgical microscopes or other optical apparatus such as otoscopes, and other medical and non-medical devices.

Turning to some general information about light, the energy distribution of light is what determines the nature of its interaction with an object, compound or organism. A common way to determine the energy distribution of light is to measure the amount or intensity of light at various wavelengths to determine the energy distribution or spectrum of the light. To make light from a light source useful for a particular purpose it can be conditioned to remove undesirable wavelengths or intensities, or to enhance the relative amount of desirable wavelengths or intensities of light.

A high signal to noise ratio and high out of band rejection enhances the spectral characteristics of different light sources or lighting environments, and also enhances fluorescence excitation, spectroscopy or clinical treatments such as photodynamic therapy.

The systems and methods, including kits and the like comprising the systems or for making or implementing the systems or methods, provide the ability to selectively, and variably, decide which colors, or wavelengths, from a light source will be projected from the system, and how strong each of the wavelengths will be. The wavelengths can be a single wavelength, a single band of wavelengths, a group of wavelengths/wavelength bands, or all the wavelengths in a light beam. If the light comprises a group of wavelengths/wavelengths bands, the group can be either continuous or discontinuous. The wavelengths can be attenuated so that the relative level of one wavelength to another can be increased or decreased (e.g., decreasing the intensity of one wavelength among a group of wavelengths effectively increases the other wavelengths relative to the decreased wavelength). This is highly advantageous because such fine control of spectral output and wavelength dependant intensity distribution permits a single lighting system to provide highly specialized light such as light for diagnosing or treating disease or activating drugs.

DEFINITIONS

The following paragraphs provide definitions of some of the terms used herein. All terms used herein, including those specifically discussed below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

A "controller" is a device that is capable of controlling a spatial light modulator, a detector or other elements of the apparatus and methods herein. A "controller" contains or is linked to computer-implemented programming. Typically, a controller comprises one or more computers or other devices comprising a central processing unit (CPU) and directs other devices to perform certain functions or actions, such as the on/off pattern of the pixels in the pixelated SLM, the on/off status of pixels of a pixelated light detector (such as a charge coupled device (CCD) or charge injection device (CID)), and/or compile data obtained from the detector, including using such data to make or reconstruct images or as feedback to control an upstream spatial light modulator. A computer comprises an electronic device that can store coded data and can be set or programmed to perform mathematical or logical operations at high speed. Controllers are well known and selection of a desirable controller for a particular aspect of the present apparatus and methods is readily achievable in view of the present disclosure.

A "spatial light modulator" (SLM) is a device that is configured to selectively modulate light. The present invention comprises one or more spatial light modulators disposed in the light path of an illumination system. A pixelated spatial light modulator comprises an array of individual pixels, which are a plurality of spots that have light passing characteristics such that they transmit, reflect or otherwise send light along a light path, or instead block the light and prevent it or interrupt it from continuing along the light path. Such pixelated arrays are well known in the art, having also been referred to as a multiple pattern aperture array, and can be formed by an array of ferroelectric liquid crystal devices, liquid crystal on silicon (LCOS) devices, electrophoretic displays, or by electrostatic microshutters. See, U.S. Pat. No. 5,587,832; U.S. Pat. No. 5,121,239; R. Vuelleumier, Novel Electromechanical Microshutter Display Device, Proc. Eurodisplay '84, Display Research Conference September 1984.

A reflective pixelated SLM comprises an array of highly reflective mirrors that are switchable between at least an on and off state, for example between at least two different angles of reflection or between present and not-present. Examples of reflective pixelated SLMs include digital micromirror devices (DMDs), liquid crystal on silicon (LCOS) devices, as well as other MicroElectroMechanical Structures (MEMS). DMDs can be obtained from Texas Instruments, Inc., Dallas, Tex., U.S.A. In this embodiment, the mirrors have three states. In a parked or "0" state, the mirrors parallel the plane of the array, reflecting orthogonal light straight back from the array. In one energized state, or a "−10" state, the mirrors fix at −10° relative to the plane of the array. In a second energized state, or a "+10" state, the mirrors fix at +100 relative to the plane of the array. Other angles of displacement are possible and are available in different models of this device. When a mirror is in the "on" position light that strikes that mirror is directed into the projection light path. When the mirror is in the "off" position light is directed away from the projection light path. On and off can be selected to correspond to energized or non-energized states, or on and off can be selected to correspond to different energized states. If desired, the light directed away from the projection light path can also be collected and used for any desired purpose (in other words, the DMD can simultaneously or serially provide two or more useful light paths).

The pattern in the RPSLM can be configured to produce two or more spectral and intensity distributions simultaneously or serially, and different portions of certain RPSLMs can be used to project or image along two or more different projection light paths.

An "illumination light path" is the light path from a light source to a target, while a "detection light path" is the light path for light emanating from the target or sample to a detector. The light includes ultraviolet (UV) light, blue light, visible light, near-infrared (NIR) light and infrared (IR) light.

"Upstream" and "downstream" are used in their traditional sense wherein upstream indicates that a given device is closer to a light source, while downstream indicates that a given object is farther away from a light source.

The discussion herein includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Turning to the figures, FIG. 1 schematically depicts a color endoscopy system 2. Computer controlled light source (CCLS) 10 is controlled by endoscopy system computerized controller 50 is disposed at a proximal end of the light guide 90 of endoscope 30. CCLS 10 emits a light beam that is directed into the illumination light guide 90 of endoscope 20. The light is conducted through the endoscope via the illumination light guide 90 to the distal tip 100 of the endoscope where it exits the endoscope and illuminates the tissue 110. A portion of the light emanating from tissue 110 is captured by the objective lens located in endoscope tip 40 and is directed to form an image of the tissue on image sensor 30, which as depicted is located at the proximal end of the endoscope 20; other locations for the image sensor 30 can also be suitable. Any suitable optical elements can be employed as the objective lens, if one is desired, such as lenses, mirrors, optical fibers or filters for the forming, mixing, imaging, collimating or other conditioning of the light. Thus, the light is passed by the objective either by transmitting the light or by reflecting the light or otherwise by acting upon the light. If desired, optical filters and other desired elements can also be provided in the primary image path, connected by mirrors, lenses or other optical components.

The optical image of the tissue is transduced by image sensor 30 to create an electrical signal representative of the image. Image sensor 30 may be a charge coupled device (CCD), complementary metal oxide semiconductor (CMOS) or charge injection device (CID) image sensor, or it may be another type of image sensor.

Image sensor 30 is operably connected via endoscope image output and image control cable 40 to the image capture system of endoscopy system controller 20. The image signal data from the image sensor 45 of endoscope 30 is transmitted to the system controller 50. Transmission of the image signal may be effected by electrical signals traveling through conducting wires, optical signals traveling through optical fibers or other optical transmission methods or it may be transmitted by wireless communication devices such as radio waves or other types of wireless devices or networks, or otherwise as desired.

The system controller 50 processes the video image and transmits as an analog or digital video image signal 60 to the image capture and image analysis sub system 210 (FIG. 2) of the computer controlled light source.

The captured digital image is stored and associated with data that identifies the relative time the image was captured and the type of illumination provided by the CCLS when the image was captured. The image processing subsystem 210 of CCLS 10 can then analyze the images captured to determine whether adjustments to the illumination light output characteristics would be advantageous and can process the captured image to adjust the image for the relative amount of illumination and then pass the processed image on via connector 70 to image display unit 80.

System controller 20 contains computer implemented programming that controls the spectral distribution and timing of the light output by the computer controlled light source 10.

Figure 2:
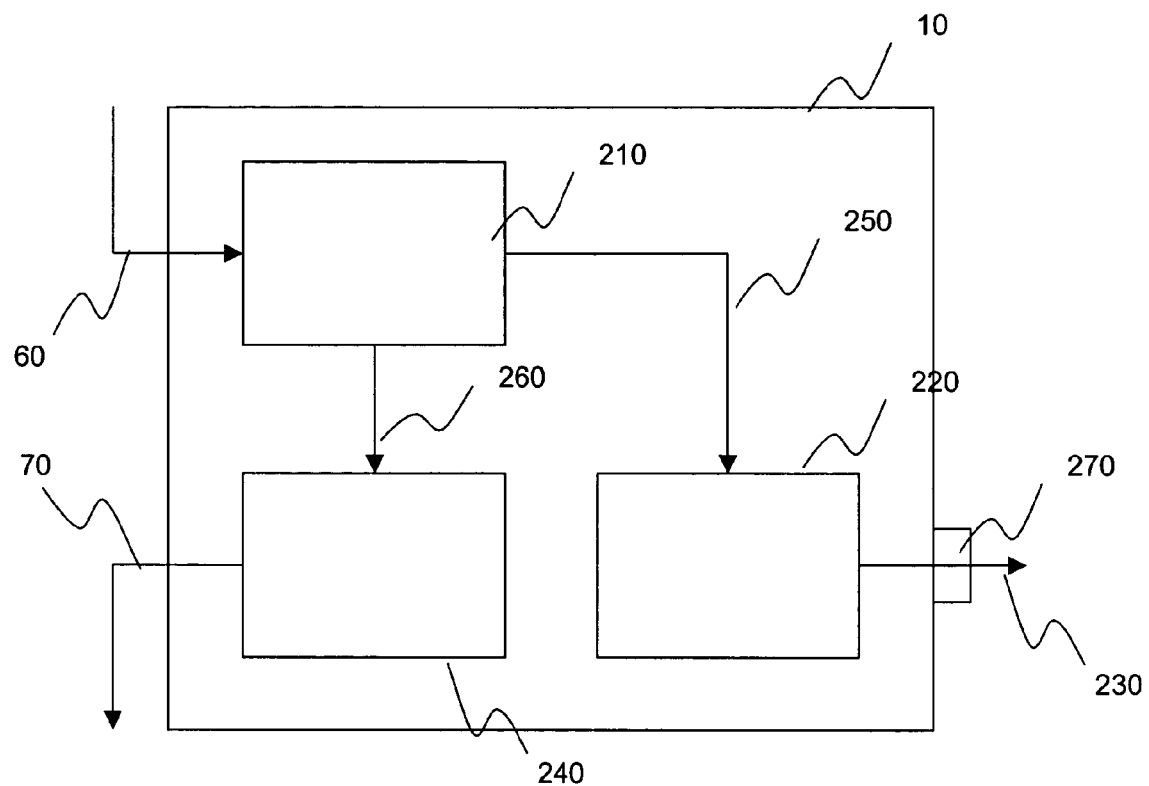
FIG. 2 provides a schematic depiction of the main components of a tunable light source with an integrated image capture device or subsystem.

Turning to FIG. 2, CCLS 10 comprises several subsystems. Image signal 60 is transmitted to image processing subsystem 210 that accepts the image signal and if desired converts it to a desired format for analysis, for example a digital image. The image is analyzed using computer implemented programming to determine if the image signal is within the optimum measurement range of the image sensor for each color channel of the image being measured. An image color channel corresponds to a specific distribution of wavelengths that may be useful for distinguishing features or enhancing information about the object being imaged. Some examples of image channels that are well known are red, green and blue image channels or cyan, yellow and magenta. The wavelength ranges corresponding to these channels are well known but can be adjusted as desired.

If an image channel is not within a desired range of the image sensor the illumination intensity can be adjusted, within the range of control to provide more or less illumination in the corresponding wavelength range. If it is determined that an adjustment to the illumination needs to be made, this is communicated via internal data communication interface 250 to lighting control module 220. Lighting control module 220 adjusts the wavelength dependent intensity of the output illumination 270 as desired and directs the output illumination 270 via endoscope light guide adapter 270 to the illumination light guide of the endoscope or to the illumination light path of the surgical microscope, or other tissue observation device.

If it is determined that an adjustment to the illumination needs to be made, this is also communicated via internal data communication interface 260 to output image processing module 240. The image data is also communicated via internal data communication interface 260 to output image processing modules 240. When lighting control module 220 adjusts the wavelength dependent intensity of the output illumination 270 the amount of the adjustment is used to determine the proportional amount that the digital image needs to be scaled to preserve the quantitative relationships between the image channels, while ensuring that the measurement is within the dynamic range of the sensor. The output image can be adjusted proportionately to preserve the optical relationships of the image channels and effectively communicate information about the tissue to the physician, surgeon or other clinical staff.

Figure 3:
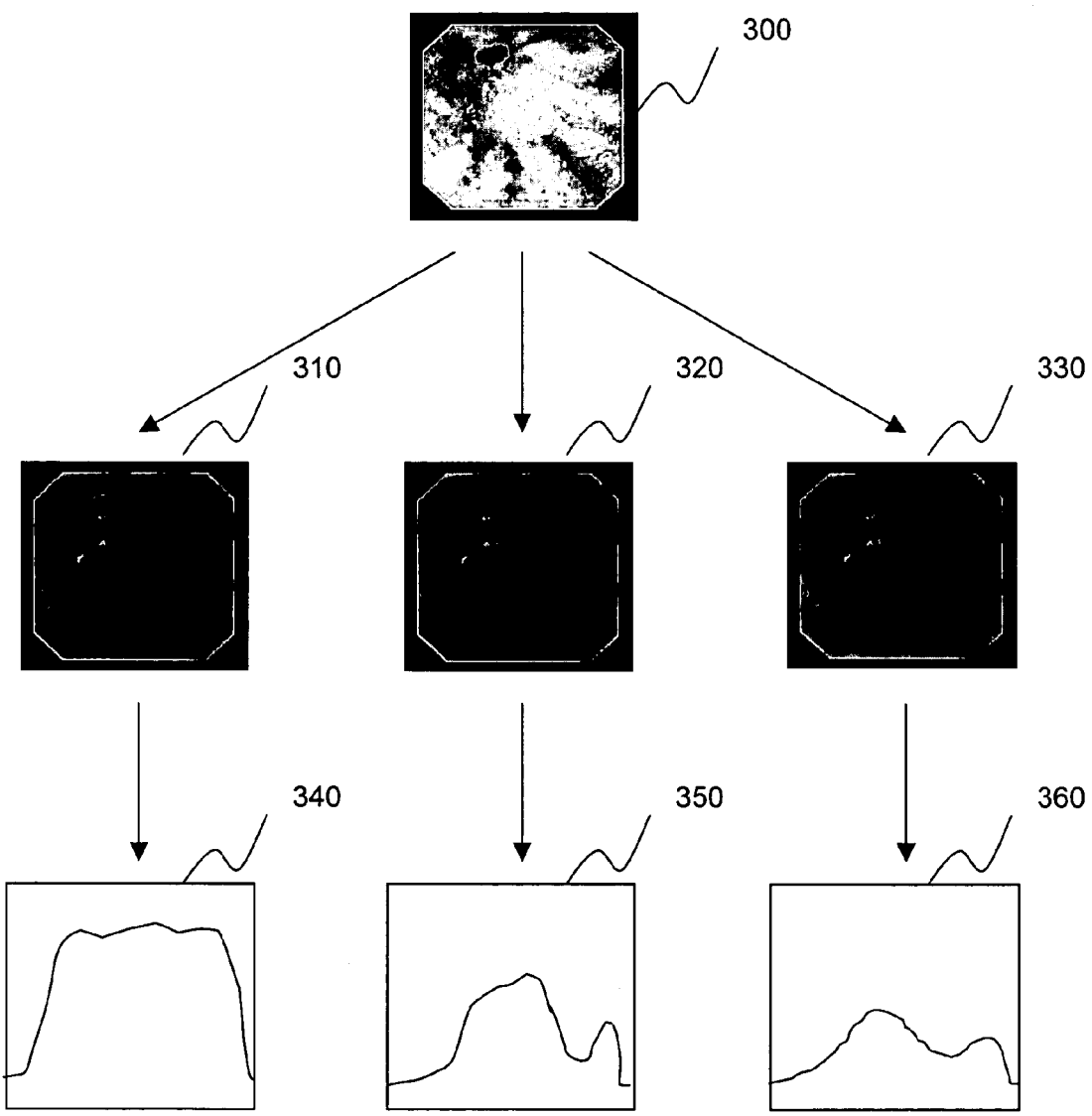
FIG. 3 provides a schematic depiction of a color video image, its red, green and blue image components and a graph representing the intensity of a horizontal video line across the center of each image.

FIG. 3 provides an example of a digital color endoscopy image 300 and its component red image channel 310, green image channel 320 and blue image channel 330. The intensity of these images is within the dynamic range of the image sensor as can be seen by the graphs representing the intensity of the pixels in a line across the middle of each of the images for the red 340, green 350 and blue 360 image channels.

Figure 4:
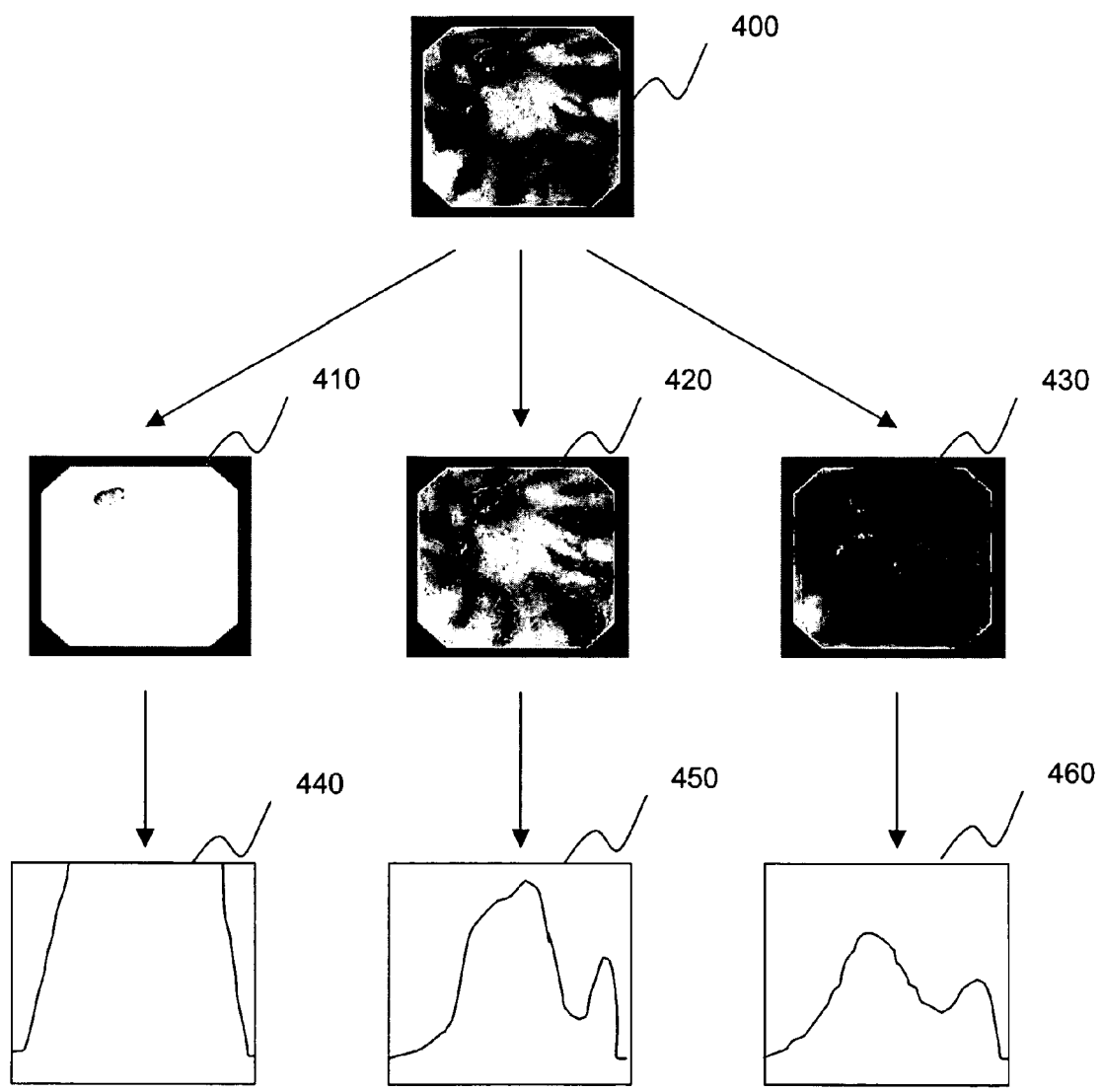
FIG. 4 is a schematic representation of a color video image with the green channel saturated.

FIG. 4 provides an example of a digital color endoscopy image 400 and its component red image channel 410, green image channel 420 and blue image channel 430. The intensity of the green 420 and blue 430 images is within the dynamic range of the image sensor, but red image 410 is saturated as can be seen by the graphs representing the intensity of the pixels in a line across the middle of each of the images for the red 440, green 450 and blue 460 image channels.

Most commercially available endoscopy image systems have the capability of attenuating the overall illumination of the light source. This can be done by adjusting the power to the lamp, or by moving a screen or other aperture in front of the output of the system to attenuate the light delivered to the illumination light guide. Often this adjustment is performed automatically by computer or electronic analysis of the image signal providing feedback to the illumination control system.

Figure 5:
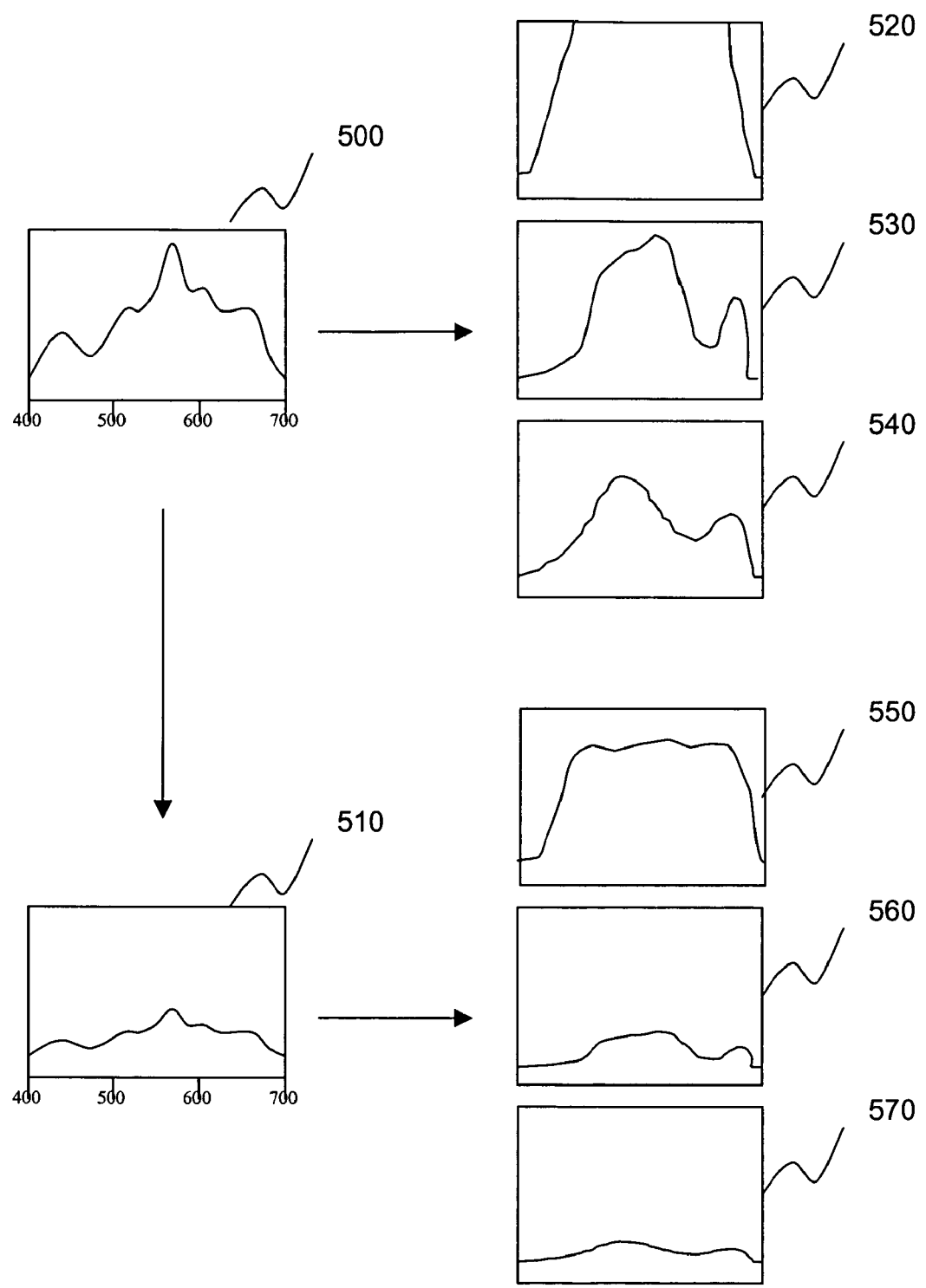
FIG. 5 is a schematic representation of the effect on the video image and color channels when image saturation triggers an illumination intensity reduction.

FIG. 5 provides a schematic representation of the effect of adjusting overall illumination intensity on the video signal. The wavelength dependent intensity distribution of illumination light 500 provided to an endoscope light guide results in saturation of the red channel as shown in graph 520 of the intensity of pixels along a line through the center of the red image channel. The green channel and the blue channel are within the dynamic range of their respective channels as shown in the graphs of a line through the center of the green channel image 530 and the blue channel image 540. When the system or the operator detects saturation of one or more of the image video channels, the illumination intensity is reduced across all wavelength channels as shown in graph 510 of the wavelength dependent intensity of the light source. The effect of this adjustment is to reduce the intensity of the red image to a range that is within the dynamic range of the image sensor for the red channel, as shown in graph 550 of the intensity of pixels along a line through the center of the red image channel. The green channel and the blue channel are now at the low end of the dynamic range of their respective channels as shown in the graphs of a line through the center of the green channel image 560 and the blue channel image 570 and are not in the optimal detection range of the image sensor.

Figure 6:
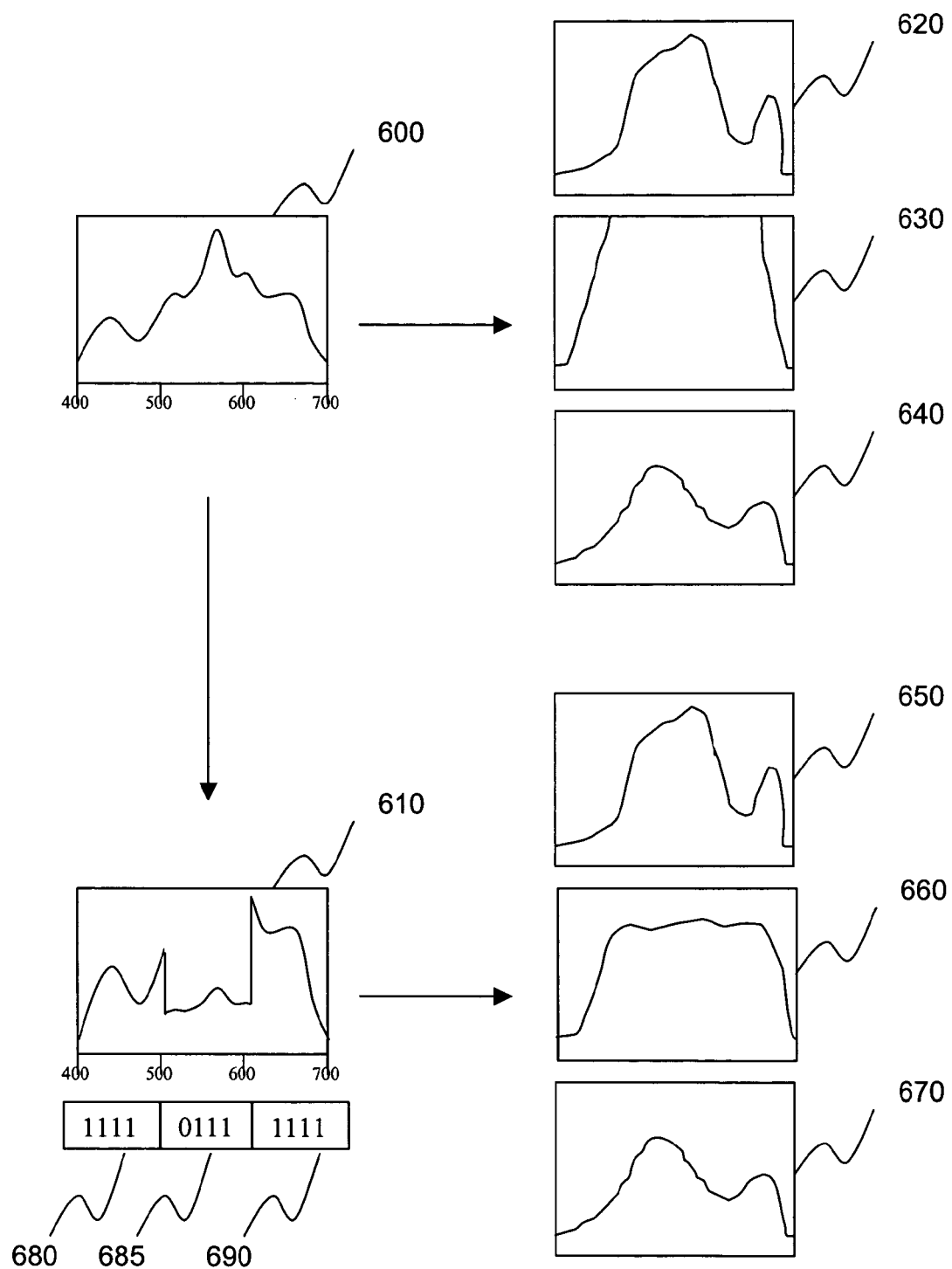
FIG. 6 is a schematic representation of the effect on the video image and color channels when image saturation triggers an illumination intensity reduction for only wavelengths of light that contribute to the signal for the saturated channel.

FIG. 6 provides an example of an endoscopy light source that provides control of the wavelength dependent intensity of illumination rather that just overall adjustment of the intensity of illumination. In FIG. 6, illumination profile characterized by a particular wavelength dependent distribution of intensity 600 illuminates a particular tissue, the intensity profiles of the red channel 620 and the blue channel 640 are within the dynamic range of the image sensor, but the green channel 630 is saturated. When the resultant image is analyzed, instead of attenuating all wavelengths, the light source attenuates only one wavelength region as shown in graph 610 of the wavelength dependent intensity distribution of the computer controlled light source. The amount of the attenuation can be adjusted and then the degree of that attenuation can be factored into the measured intensity for that channel of the image, to be used when digitally reconstructing an enhanced dynamic range image. The digital attenuation factor for the red channel 680, the green channel 685 and the blue channel 690 can be recorded as binary intensity values which can be combined with digital binary image data. The intensity of these images is now within the dynamic range of the image sensor as can be seen by the graphs representing the intensity of the pixels along a line across the middle of each of the images for the red 650, green 660 and blue 670 image channels.

Figure 7:
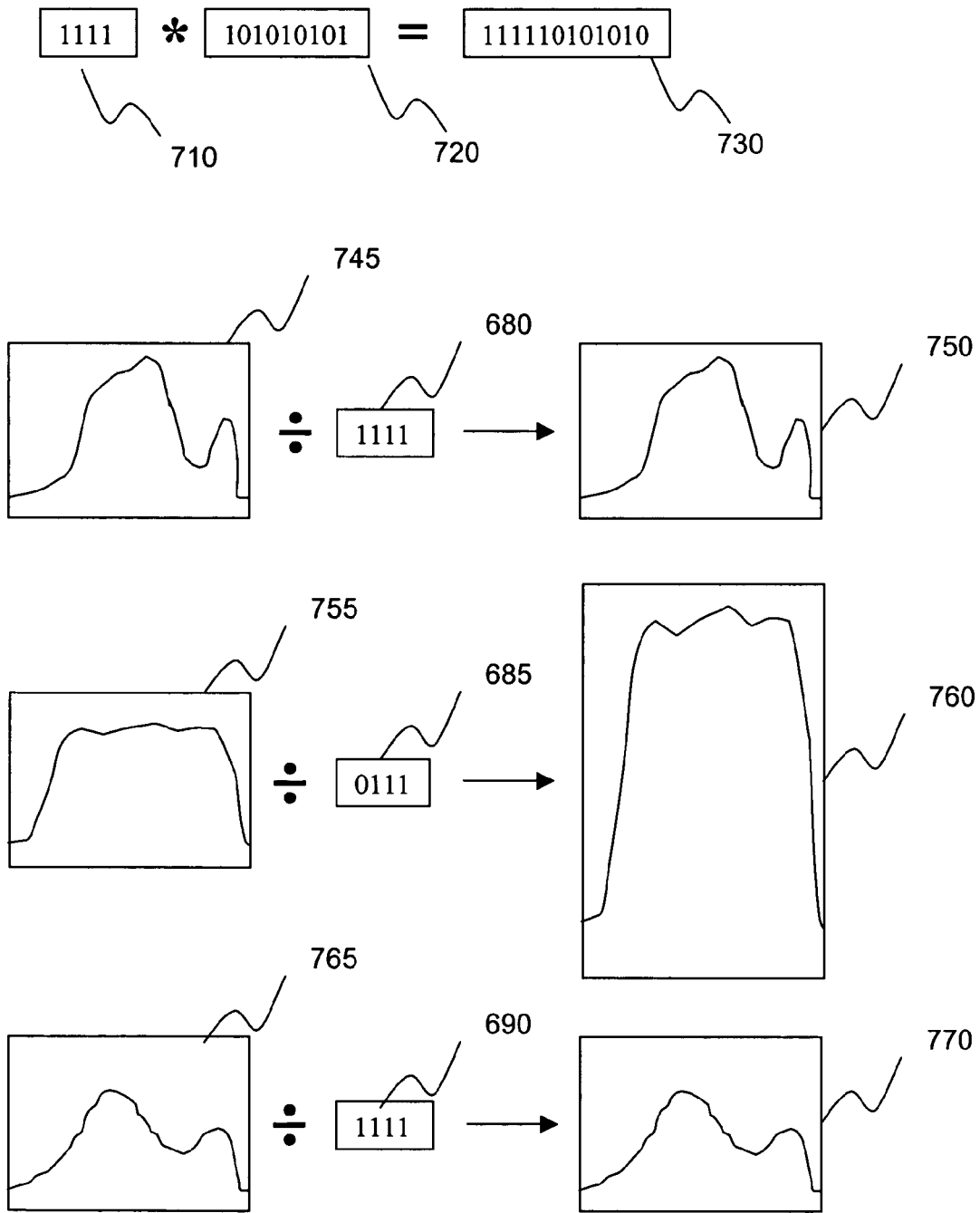
FIG. 7 is a schematic representation of the effect on the video image signal when the output image channel that has had illumination attenuated has its signal restored by multiplying the signal by the attenuation factor.
Figure 8:
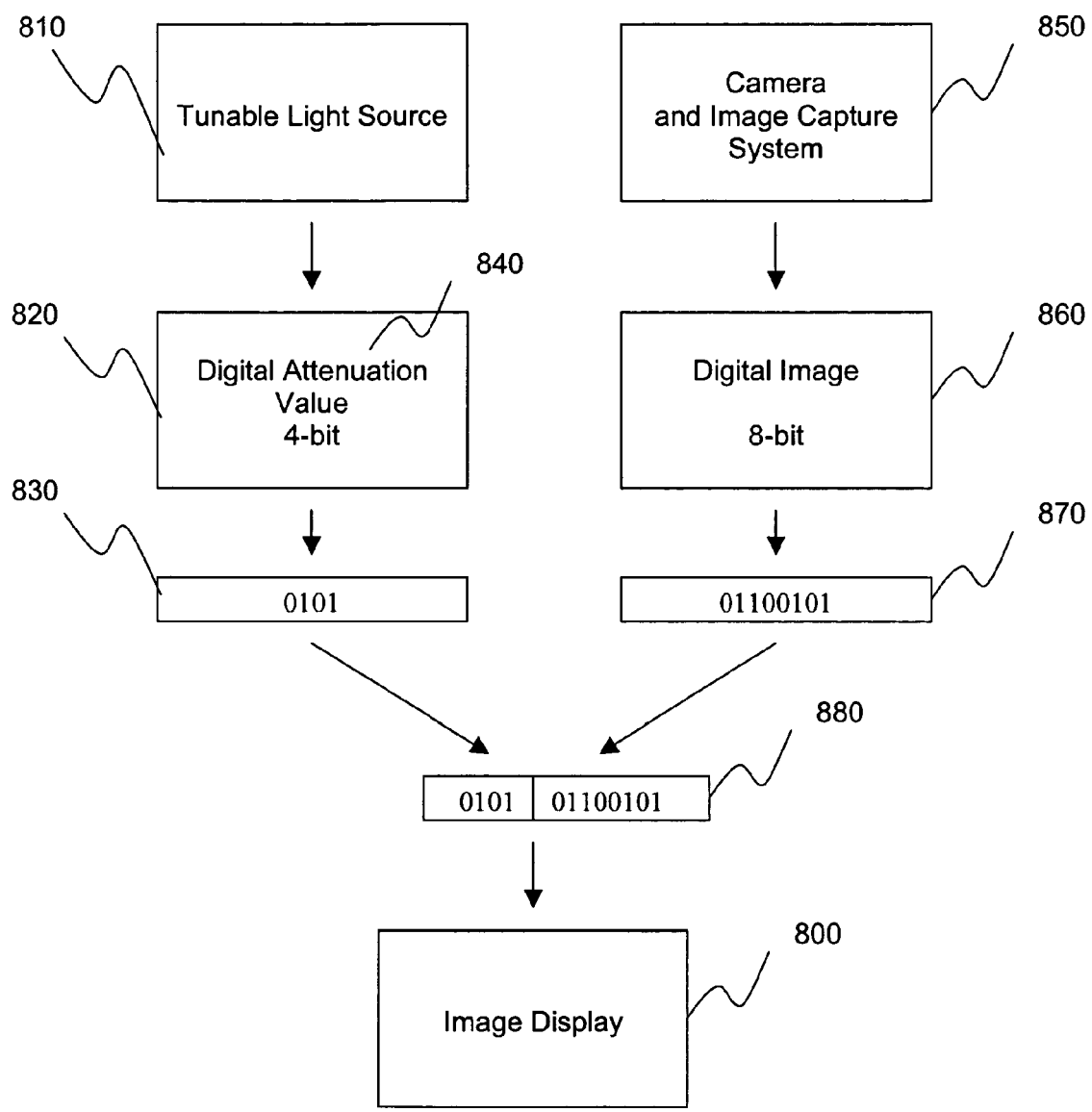
FIG. 8 is a schematic representation illustrating the dynamic range of a digital image and the relative contribution of the dynamic range of the light source and the dynamic range of the digitized image from the image sensor.

Turning to FIGS. 7 and 8, the output image processing module 240 can process the image to incorporate the additional dynamic range information provided by the control of illumination intensity by combining the information in several ways. FIG. 7 shows the combination of an illumination light source with 16 levels (4 bit) of illumination intensity control being combined with an image with 256 levels (8 bit) of measurable image intensity. These can be represented in binary notation by a 4 bit number and an 8 bit number. Multiplying the range of illumination by the range of detection provides a theoretical dynamic range of 12 bits or 5096 levels of intensity. The 4 bit illumination range and 8 bit image range mentioned above are exemplary. Actual values for illumination range can be any range of control and measurement that is possible for the light source and imaging device being used. For example, the light source might provide 6, 8, 12 or 16 bits of adjustment, and the detector can similarly provide 6, 8, 12 or 16 bits of detection sensitivity.

FIG. 7 shows how the exemplary 4 bit digital illumination range of the light source 710 can be combined with the exemplary 8 bit digital image range of the detector 720 to produce a digital image with 12 bits of range 730. By multiplying the 8 bit image pixel value by the 4-bit illumination range and then dividing by the actual illumination value one can calculate the actual 12-bit value within the 12-bit dynamic range image. In FIG. 7, the red channel image values from FIG. 6 have been multiplied by the illumination range to produce 12 bit image intensity values 745. These values are then divided by actual illumination value 680 to produce the red digital output image values 750. Green channel 765 is divided by actual illumination value 685 to produce the green digital output image values 760. Green channel 765 is divided by actual illumination value 690 to produce the digital output image values 770. For the green channel and digital output image values 760, the height of the graph has been increased two-fold to account for the halving of the illumination intensity used in the green channel, which compensated for the saturation when the green illumination intensity was the same as the intensity of the red and blue channels.

The resultant values have sufficient dynamic range and accuracy to provide improved display and image processing of the resultant output images.

FIG. 8 provides a schematic flow chart representation of how the controllable illumination range 800 of the light source can be combined with the measurement range 802 of the imaging device to provide expanded dynamic range imaging. Briefly, tunable light source 810 (CCLS) selectably, variably controls the wavelength and intensity of the light from the light source 810. Such control can be from a feedback loop that informs the computer controlling the tunable light source 810 whether the response from a sample within a given wavelength range or band is too high or too low to be meaningfully measured, from a user, or otherwise as desired. The tunable light source 810 is then adjusted 820 until the response from the tissue is appropriate. In FIG. 8, the light is attenuated according to a 4-bit value (other levels of attenuation or increased illumination as desired are also possible) indicated as a digital attenuation value 840. Such value can also be represented in binary form to provide a digital illumination value 830. Generally working in concert with the illumination range 800, measurement range 802 comprises a detection system 850 having a given range of measurement values 860, which in the example given is an 8-bit range (other levels of measurement as desired are also possible), which can be expressed in binary form to provide a digital measurement value 870. The different measurement values 830, 870 are then combined to provide a full image value 880, which as indicated can also be expressed in binary form. This full image value 880 then provides an image display 890 having an enhanced dynamic range, here a 12 bit (4 bit×8 bit) range.

Figure 9:
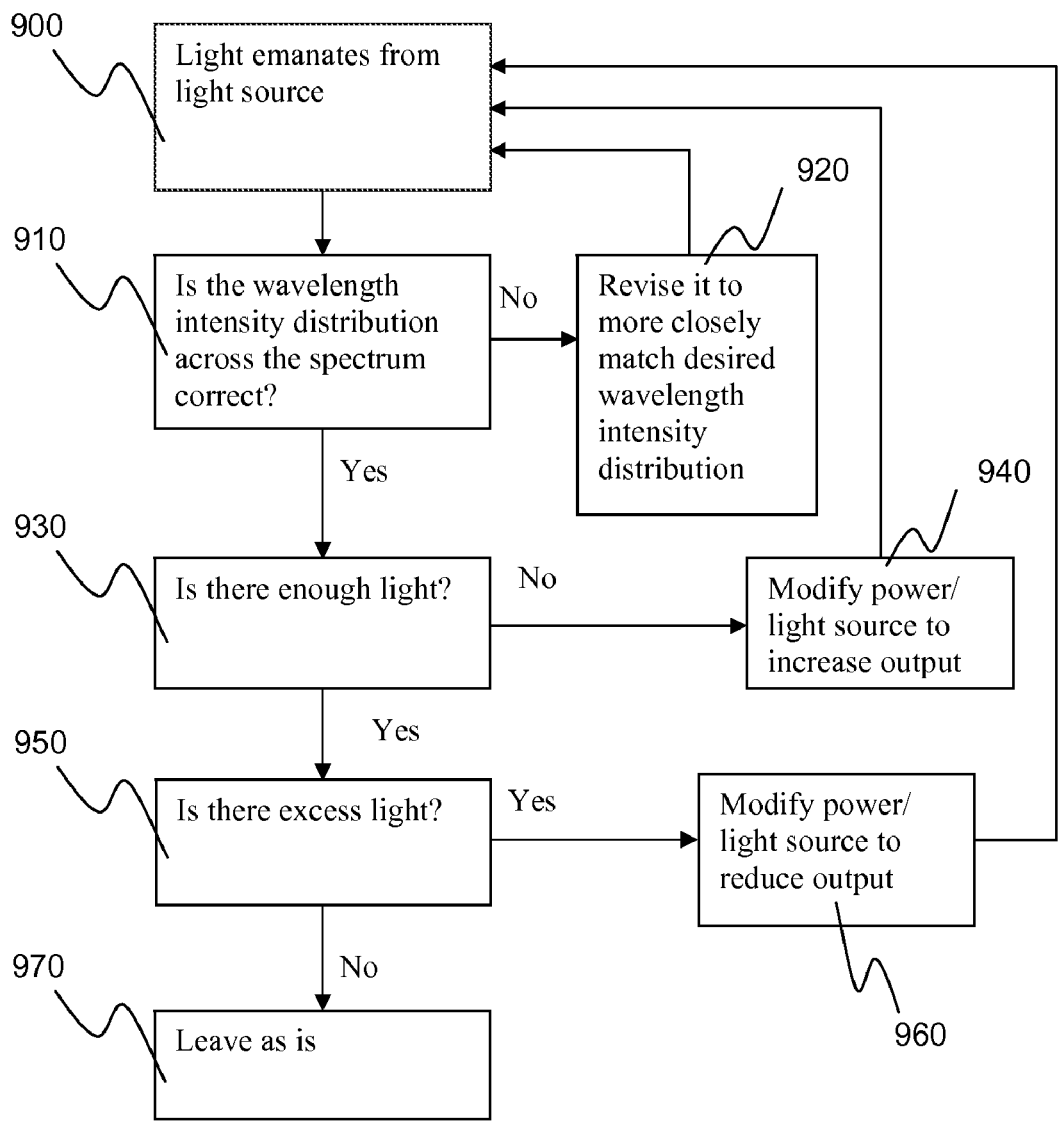
FIG. 9 is a flowchart depicting an embodiment of the methods herein.

In FIG. 9, light emanates from light source as in box 900, the question is then asked in 910, "Is the wavelength intensity distribution across the spectrum correct?" If no, then in 920 the emanating light is revised to more closely match the desired wavelength intensity distribution. If yes, then in 930 the question is asked, "Is there enough light?"

In 940, if the answer to 930 is "no", then the power and/or light source is modified to increase the output. If the answer to 930 is "yes", then in 950 the question is asked, "Is there excess light?" If the answer to 950 is "yes", then in 960 the power and/or light source is modified to reduce the output. Conversely, if the answer to 950 is "no", then in 970 the power and/or light source is left "as is".

Thus, in some aspects the optical imaging systems having good dynamic range comprise a tunable light source configured to emit illumination light comprising a variable selected spectral output and a variable wavelength dependent intensity distribution. The light source can be configured to independently increase or decrease the variable selected spectral output and the variable wavelength dependent intensity distribution as desired. A sensor configured to detect light emanating from the target tissue and transmit a signal representing at least the spectral distribution and wavelength dependent intensity distribution of the emanating light to a processor, and a controller operably connected to the light source, the sensor and the processor, the controller containing computer-implemented programming that can be configured to coordinate the light source, sensor and processor such that the programming varies the selected spectral output and wavelength dependent intensity distribution of the illumination light to provide a compensatory illumination light configured to compensate for oversaturation or underexposure in a specific wavelength distribution in the signal without substantially changing acceptable wavelength distributions, and the computer-implemented programming can be configured to combine data about the variation of the light source with the data about the signal to provide an enhance dynamic range for the system compared to the sensor alone. The system can be a part of, attached to (permanently or temporarily) or embodied in an endoscope, otoscope, surgical microscope or other medical or non-medical system.

The tunable light source can comprise a source of light, and a tunable filter comprising a spectrum former and a pixelated spatial light modulator (SLM) located downstream from and optically connected to the spectrum former, the pixelated SLM configured to pass the desired light. The SLM can be a reflective or transmissive pixelated SLM. The pixelated SLM can be configured to provide first and second pixelated SLM regions disposed substantially side-by-side with a light blocking barrier therebetween, and the system further can comprise at least one optical element located and configured to transmit light from the first pixelated SLM region to the second pixelated SLM region. The tunable light source can also comprise an acousto-optic tunable filter (AOTF) in place of or in addition to the SLM. The tunable light source can comprise at least two tunable filters configured in series to eliminate virtually all unwanted light.

The sensor can be disposed at the distal end and can be a monochromatic or color sensor. The system can further comprise computer-implemented programming configured to coordinate the light source, sensor and processor such that the light source provides over time a plurality of different desired wavelength bands of illumination light each having a selected, substantially pure, variable distribution and intensity, the monochromatic sensor detects light intensity emanating from the target tissue to provide a detected light intensity for each of the desired wavelength distributions, and the processor associates the detected light intensity for each of the bands with a selected color suitable for display on a display device. The system can be configured such that the compensatory illumination light can be attenuated in substantially only a single wavelength band compared to the illumination light, which can be for example one of red, blue or green, or one of cyan, yellow or magenta or other band as desired. The compensatory illumination light can also be attenuated in a plurality of wavelength bands.

The illumination light can comprise at least one band of fluorescence excitation (or other excitation light) illumination light. If desired, the system further can comprise at least one long pass filter configured to block substantially all of the fluorescence excitation illumination band that reflects back to the sensor, which can be any of a charge coupled device (CCD), a complementary metal oxide semiconductor (CMOS), a charge injection device (CID), and a photodiode array or other sensor as desired. The system can also have a display device. The endoscope can be flexible or non-flexible, and the illumination can comprise or consists essentially of visible light, ultraviolet (UV) light and infrared (IR) light. The system can be configured to provide different intensities for at least one wavelength band of illumination light by varying the amount of time and/or attenuating the different desired wavelength bands can be emitted from the endoscope.

The spectral output and a wavelength dependent intensity distribution can also be configured for disease treatment, photodynamic therapy, for disease diagnosis, to enhance contrast for detection or discrimination of a desired object in the target tissue or for other purposes as desired. The processor can be the controller.

In other aspect, the methods herein include making and using the systems and devices discussed herein. For example, the methods can comprise obtaining an image of a target having good dynamic range comprising a) emitting illumination light from a tunable light source configured to emit illumination light comprising a variable selected spectral output and a variable wavelength dependent intensity distribution, The light source can be configured to independently increase or decrease the variable selected spectral output and the variable wavelength dependent intensity distribution as desired, to illuminate a target, b) sensing emanating light from the target via a sensor that measures the spectral distribution and wavelength dependent intensity distribution of the emanating light, a c) determining whether the emanating light saturates, overexposes or underexposes sensing elements of the sensor, d) where the emanating light saturates, overexposes or underexposes sensing elements of the sensor, selectively adjusting the selected spectral output and wavelength dependent intensity distribution of the illumination light to provide a compensatory illumination light configured to compensate for the oversaturation or underexposure in a specific wavelength distribution in the signal without substantially changing acceptable wavelengths, and e) combining the data about the adjusting of the light source with data from the signal to provide an enhanced dynamic range compared to the sensor alone.

From the foregoing, it will be appreciated that, although specific embodiments have been discussed herein for purposes of illustration, various modifications may be made without deviating from the spirit and scope herein. Accordingly, the systems, methods, etc., herein include such modifications as well as all permutations and combinations of the subject matter set forth herein and is not limited except as by the appended claims.

What is claimed is:

1. A method of obtaining an image of a target having good dynamic range comprising:
   a) emitting illumination light from a tunable light source configured to emit illumination light comprising a variable selected spectral output and a variable wavelength dependent intensity distribution, wherein the light source is configured to independently increase or decrease the variable selected spectral output and the variable wavelength dependent intensity distribution as desired, to illuminate a target;
   b) sensing emanating light from the target via an image sensor configured to detect light emanating from a target and transmit an image of the target to a processor; and,
   c) determining whether the emanating light saturates, overexposes or underexposes sensing elements of the image sensor;
   d) where the emanating light saturates, overexposes or underexposes sensing elements of the image sensor, selectively adjusting the selected spectral output and wavelength dependent intensity distribution of the illumination light to provide a compensatory illumination light configured to compensate for the oversaturation or underexposure in a specific wavelength distribution in the image without substantially changing acceptable wavelengths; and,
   e) combining data about the adjusting of the light source with data from the image to provide an enhanced dynamic range compared to the image sensor alone.

2. The method of claim 1 wherein the target is a target tissue and the method is implemented via an endoscope.

3. The method of claim 2 wherein the image sensor is disposed at a distal end of the endoscope.

4. The method of claim 2 wherein the image sensor is a monochromatic image sensor.

5. The method of claim 4 wherein the method further comprises using computer-implemented programming configured to coordinate the light source, image sensor and processor such that the light source provides over time a plurality of different desired wavelength distributions of illumination light each having a selected, substantially pure, variable distribution and intensity, the monochromatic image sensor detects light intensity emanating from the target to provide a detected light intensity for each of the desired wavelength distributions, and the processor associates the detected light intensity for each band with a selected color suitable for display on a display device.

6. The method of claim 2 wherein the compensatory illumination light is attenuated in a plurality of wavelength bands compared to the illumination light.

7. The method of claim 2 wherein the illumination light comprises at least one band of fluorescence excitation illumination light and at least one long pass filter blocks substantially all of the fluorescence excitation illumination band that reflects back to the image sensor.

8. The method of claim 2 wherein the endoscope is a surgical microscope or an otoscope.

9. The method of claim 2 wherein the method further comprises a displaying a high dynamic range image on a display device.

10. The method of claim 2 wherein a body of the endoscope is non-flexible.

11. The method of claim 2 wherein a body of the endoscope is flexible.

12. The method of claim 2 further comprising providing different intensities for at least one wavelength distribution of illumination light by varying the amount of time the different desired wavelength distributions are emitted from the endoscope.

13. The method of claim 2 further comprising providing different intensities for at least one wavelength distribution of illumination light by attenuating the amount of light emitted for the different desired wavelength distributions.

14. The method of claim 2 wherein computer implemented programming selectively also provides a spectral output and a wavelength dependent intensity distribution that substantially mimics a spectral output and a wavelength dependent intensity distribution of output energy for disease treatment.

15. The method of claim 2 wherein the computer implemented programming selectively also provides a spectral output and a wavelength dependent intensity distribution that substantially mimics a spectral output and a wavelength dependent intensity distribution of output energy for photodynamic therapy.

16. The method of claim 2 wherein the computer implemented programming selectively also provides a spectral output and a wavelength dependent intensity distribution that substantially mimics a spectral output and a wavelength dependent intensity distribution of output energy for disease diagnosis.

17. The method of claim 2 wherein the computer implemented programming selectively also provides a spectral output and a wavelength dependent intensity distribution that substantially mimics a spectral output and a wavelength dependent intensity distribution of output energy to enhance contrast for detection or discrimination of a desired object in the target.

* * * * *